(12) United States Patent
Drake et al.

(10) Patent No.: US 12,329,411 B2
(45) Date of Patent: Jun. 17, 2025

(54) TETHER ASSEMBLIES FOR MEDICAL DEVICE RETRIEVAL SYSTEMS

(71) Applicant: Medtronic, Inc., Minneapolis, MN (US)

(72) Inventors: Ronald A. Drake, St. Louis Park, MN (US); Lester O. Stener, Hudson, WI (US); Brian P. Colin, Anoka, MN (US); Zhongping C. Yang, Woodbury, MN (US); Thomas A. Anderson, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 265 days.

(21) Appl. No.: 17/807,081

(22) Filed: Jun. 15, 2022

(65) Prior Publication Data

US 2023/0017564 A1  Jan. 19, 2023

Related U.S. Application Data

(60) Provisional application No. 63/221,616, filed on Jul. 14, 2021.

(51) Int. Cl.
*A61B 17/34* (2006.01)
*A61B 17/00* (2006.01)
(Continued)

(52) U.S. Cl.
CPC .......... *A61B 17/3468* (2013.01); *A61B 2017/00323* (2013.01); *A61M 25/005* (2013.01);
(Continued)

(58) Field of Classification Search
CPC ..... A61B 17/3468; A61B 2017/00323; A61M 25/005; A61M 25/0082; A61N 1/362; A61N 2001/0578
See application file for complete search history.

(56) References Cited

U.S. PATENT DOCUMENTS

| 9,421,035 B2 | 8/2016 | Hendrick |
| 9,993,648 B2 | 6/2018 | Kelly et al. |

(Continued)

FOREIGN PATENT DOCUMENTS

| WO | 2019166230 A1 | 9/2019 |
| WO | 2020187666 A1 | 9/2020 |

OTHER PUBLICATIONS

Sridharan, "New Wireless Pacemaker Implanted Without Surgery, Found Safe in Clinical Study," Medgadget, Sep. 11, 2015, 3 pp.

(Continued)

*Primary Examiner* — Tan-Uyen T Ho
*Assistant Examiner* — Cherie M Poland
(74) *Attorney, Agent, or Firm* — Shumaker & Sieffert, P.A.

(57) ABSTRACT

In some examples, a system includes a catheter comprising an elongated shaft defining a lumen, and a tether assembly. The tether assembly may include an elongate body, a tether head assembly attached to a distal end of the elongate body, where the tether head assembly includes an attachment mechanism configured to releasably attach to an attachment member of a medical device, and a positioning element fixedly positioned over the elongate body and configured to align the attachment mechanism with the attachment member when the tether head assembly is extended distally out of the lumen. The positioning element may include a distal end, a proximal end, and a length between the distal end and proximal end that is less than a length of the elongate body. The tether head assembly, elongate body, and positioning element may be movable within the lumen of the elongated shaft.

20 Claims, 9 Drawing Sheets

(51) Int. Cl.
*A61M 25/00* (2006.01)
*A61N 1/05* (2006.01)
*A61N 1/362* (2006.01)

(52) U.S. Cl.
CPC .................. *A61M 25/0082* (2013.01); *A61N 2001/0578* (2013.01); *A61N 1/362* (2013.01)

(56) References Cited

U.S. PATENT DOCUMENTS

| | | | |
|---|---|---|---|
| 10,124,163 | B2 | 11/2018 | Ollivier et al. |
| 10,238,864 | B2 * | 3/2019 | Anderson .......... A61N 1/37205 |
| 10,420,932 | B2 | 9/2019 | Schmidt et al. |
| 11,931,567 | B2 * | 3/2024 | Drake ................ A61N 1/37512 |
| 2012/0095539 | A1 | 4/2012 | Khairkhahan et al. |
| 2018/0207430 | A1 | 7/2018 | Soltis et al. |
| 2020/0345396 | A1 | 11/2020 | Rickheim et al. |
| 2020/0353242 | A1 * | 11/2020 | Drake ................ A61N 1/3756 |
| 2020/0353243 | A1 | 11/2020 | Drake et al. |
| 2020/0360704 | A1 | 11/2020 | Kabe et al. |
| 2020/0367931 | A1 | 11/2020 | Rickheim et al. |
| 2021/0016056 | A1 * | 1/2021 | Drake ................ A61M 25/005 |
| 2021/0030439 | A1 | 2/2021 | Drake et al. |

OTHER PUBLICATIONS

International Preliminary Report on Patentability from International Application No. PCT/US2022/034895 dated Jan. 16, 2024, 6 pp.
International Search Report and Written Opinion of International Application No. PCT/US2022/034895 dated Sep. 27, 2022, 8 pp.
Response to Communication Pursuant to Rules 161(1) and 162 EPC dated Apr. 24, 2024, from counterpart European Application No. 22744073.2, filed Oct. 17, 2024, 11 pp.

* cited by examiner

TETHER ASSEMBLIES FOR MEDICAL DEVICE RETRIEVAL SYSTEMS

This application claims the benefit of U.S. Provisional Application Ser. No. 63/221,616 (filed Jul. 14, 2021), which is entitled "TETHER ASSEMBLIES FOR MEDICAL DEVICE RETRIEVAL SYSTEMS" and is incorporated by reference herein in its entirety.

TECHNICAL FIELD

This disclosure relates generally to medical devices, and, more particularly, to systems for retrieving medical devices.

BACKGROUND

Some types of implantable medical devices (IMDs), such as cardiac pacemakers or implantable cardioverter defibrillators systems, may be used to provide cardiac sensing and therapy for a patient via one or more electrodes. Some IMDs include an implantable pulse generator that includes a housing that encloses electronic components, which may be configured to be implanted subcutaneously in the chest of the patient or within a chamber of a heart of the patient, as examples. IMDs having a pulse generator that is configured to be implanted within a chamber of the heart may be referred to as an intracardiac device or a leadless implantable medical device. A medical device retrieval system including a retrieval catheter may be used to retrieve an intracardiac device transvenously from an implant site within a heart of a patient. The intracardiac device and medical device retrieval system then may be withdrawn from the patient.

SUMMARY

In general, this disclosure is directed to examples of tether assemblies of medical device retrieval systems and to techniques using such tether assemblies. Example tether assemblies may include a distal tether head assembly with an attachment mechanism configured to releasably attach to an attachment member of a medical device, e.g., an intracardiac device. Additionally, a tether assembly of a medical device retrieval system may include an elongate body between the distal tether head assembly and a proximal tether handle assembly. Additionally, a tether assembly of a medical device retrieval system may include a positioning element attached to the elongate body and/or the tether head assembly and configured to align the attachment mechanism of the tether head assembly with the attachment member of the medical device. The positioning element may include one or more components configured to maintain the alignment of the attachment mechanism with the attachment member while the tether head assembly extends towards attachment member. The techniques may include positioning a cup of a medical device retrieval system around a medical device and attaching the tether head assembly to the medical device within the cup, enabling removal of the medical device from the treatment site.

The retrieval system may include a catheter and a tether assembly. The catheter may comprise an elongated shaft defining a lumen. The tether assembly may comprise an elongate body, a tether head assembly attached to a distal end of the elongate body, and a positioning element fixedly positioned over the elongate body. The tether head assembly may comprise an attachment mechanism configured to releasably attach to an attachment member of a medical device. The positioning element may be configured to align the attachment mechanism with the attachment member when the tether head assembly is extended distally out of the lumen. The positioning element may comprise a distal end, a proximal end, and a length therebetween. The tether head assembly, elongate body, and positioning element may be movable within the lumen of the elongated shaft.

In some examples, the positioning element may be configured to position the tether head assembly concentrically within the elongated shaft, or to position the tether head assembly concentrically with a cup on a distal end of the catheter shaft when the tether head assembly and positioning element are at least partially extended distally out of the lumen. In some examples, the positioning element comprises a number of coils surrounding the elongate body, as well as the tether head assembly, where an inner diameter of the coils is approximately equal to an outer diameter of the tether head assembly or elongate body and an outer diameter of the coils is approximately equal to an inner diameter of the elongated shaft. As the tether head assembly extends outwards from the distal end of the elongated shaft and into the cup, a distal portion of the coils extends with the tether head assembly, while a proximal portion of the coils remains within a portion of the distal end of the elongated shaft. The body of the coils may hold the tether head assembly in alignment with an attachment member of a medical device within the cup.

In this manner, the tether assemblies described herein may reduce the time and complexity associated with a procedure to retrieve the medical device. In some examples, the tether assemblies described herein may reduce patient discomfort and a possibility of contamination of the medical device or other objects within the surgical field by reducing the amount of time that a catheter is within the body of the patient. In some examples, the tether assemblies described herein may provide one or more advantages to the functionality, reliability, robustness, manufacturability, and cost associated with such tether assemblies.

In another example, a method for using a tether assembly of a medical device retrieval system comprises positioning a distal end of a shaft of a catheter in close proximity with at least a portion of a medical device, including an attachment member; advancing a tether head assembly of a tether assembly out of a lumen defined by the shaft, wherein the tether head assembly comprises an attachment mechanism, and wherein the tether assembly comprises an elongate body, the tether head assembly at the distal end of the elongate body, and a positioning element fixedly positioned over the elongate body and configured to align the attachment mechanism with the attachment member when the tether head assembly is extended distally out of the lumen; releasably attaching an attachment mechanism of the tether head assembly to the attachment member of the medical device; and disengaging the medical device from tissue of a patient using the attachment member.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes example medical device retrieval systems. Such medical device retrieval systems may include a tether assembly comprising a tether head assembly, tether handle assembly, a positioning element, and an elongate body. The tether head assembly is attached to the elongate body and configured to releasably retain an attachment member of a medical device (e.g., an intracardiac device) via an attachment mechanism connected to a pull wire. In some examples, a tether handle assembly is configured to retain the pull wire attached to the tether head assembly. In some examples a positioning element is configured to align the attachment mechanism of the tether head assembly with the attachment member of the medical device. The tether handle assembly may include an actuator configured to transmit force to the tether head assembly via the pull wire and enable attachment of the attachment member of a medical device to the attachment mechanism of the tether head assembly at a treatment site within a patient. Once attached, the tether head assembly may be used to extract the medical device from patient tissue.

Although the example tether assemblies are generally described herein as being configured for retrieving an implantable medical device (IMD) from within the heart, e.g., an intracardiac pacemaker, it should be understood that any of the example tether assemblies described herein alternatively may be configured for retrieving medical devices implanted in other locations, other types of medical devices, or other types of devices that may or may not be implanted within a patient.

Figure 1:
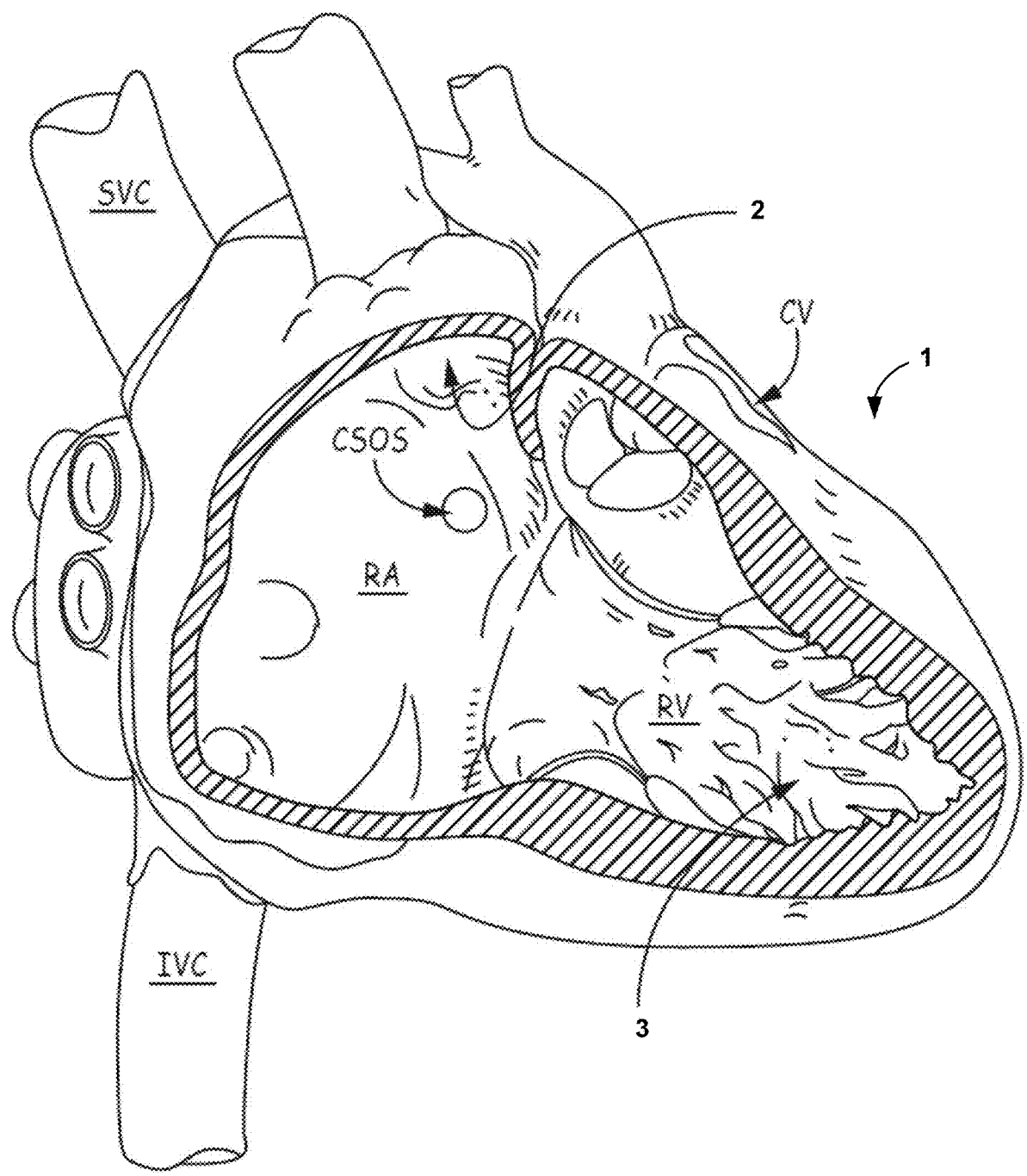
FIG. 1 is a conceptual drawing illustrating portions of patient anatomy including potential implant sites for an implantable medical device (IMD).

FIG. 1 is a conceptual drawing illustrating portions of patient anatomy including potential implant sites for an IMD. For example, an IMD may be implanted on or within heart 1 of a patient, such as within an appendage 2 of a right atrium (RA), within a coronary vein (CV) via a coronary sinus ostium (CSOS), or in proximity to an apex 3 of a right ventricle (RV). In other examples, an IMD may be implanted on other portions of heart 1 or implanted in locations other than heart 1, such as any suitable implant site in a body of the patient. FIG. 1 also illustrates an inferior vena cava (IVC) and superior vena cava (SVC).

Figure 2:
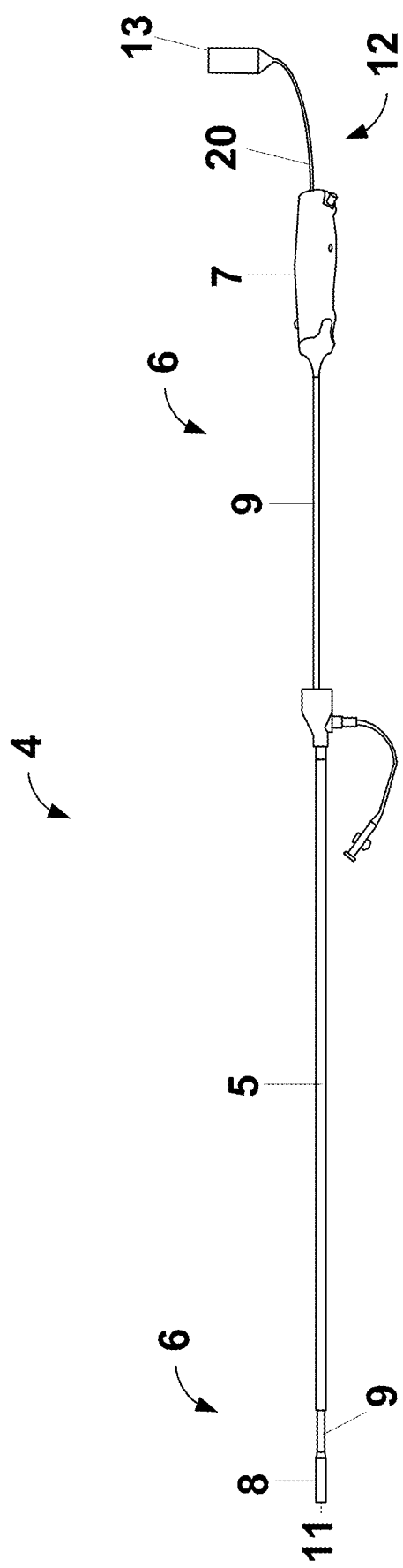
FIG. 2 is a plan drawing illustrating an example medical device retrieval system for retrieving an IMD from a location within a heart.

FIG. 2 is a plan drawing illustrating an example medical device retrieval system 4 for retrieving an IMD (not shown in FIG. 1) from a location within heart 1. Although described herein in the context of retrieving an IMD from the vasculature, e.g., heart 1, the devices, systems, and techniques of this disclosure may be used to retrieve an IMD from any anatomical location.

System 4 includes an introducer 5, a retrieval catheter 6, and a tether assembly 12. Introducer 5 is an elongated member defining an interior lumen. Introducer 5 is configured to be inserted, such as by a physician, into a vasculature of a patient to provide a rigid channel, via the interior lumen, through which to retrieve a medical instrument, device, or deliver a therapy.

Retrieval catheter 6 is configured to be inserted through the lumen of introducer 5 to retrieve an IMD within the vasculature. Retrieval catheter 6 includes an elongated shaft 9, a handle 7, and a device cup or chamber 8. Handle 7 is disposed at a proximal end of shaft 9, and may include one or more elements (such as buttons, switches, etc.) configured to control the motion or function of the distal end of shaft 9.

Device cup 8 is disposed at a distal end of shaft 9. Device cup 8 includes a hollow cylindrical body configured to house and support an IMD (e.g., IMD 10 described with respect to FIG. 3) while the IMD is being retrieved from a vasculature of a patient. For example, a physician may insert the distal end of retrieval catheter 6, including device cup 8, through the lumen of introducer 5, which is disposed within a vasculature of a patient. Once device cup 8 has extended through the distal end of introducer 5 and reached an implant site within the patient, the physician may position device cup 8, through distal opening 11, around an IMD implanted within the patient. In some examples, a physician may position cup 8 around an IMD through use of a snare as described below. A tether head assembly and positioning element (not shown in FIG. 2) may assist a physician to disengage the IMD from the patient's tissue at the implant site, after which the IMD and retrieval catheter 6 may be withdrawn proximally through introducer 5. In some examples, the IMD is repositioned and implanted at a new implant site within the patient rather than fully withdrawn, after which retrieval catheter 6 may be withdrawn.

Tether assembly 12 extends through a lumen defined by retrieval catheter 6, e.g., including handle 7 and shaft 9. Tether assembly 12 defines an elongate body 20, a tether handle assembly 13 at a proximal end of elongate body 20, and a tether head assembly 18 (FIG. 3) at a distal end of elongate body 20. Elongate body 20 may have sufficient length that a clinician may advance tether assembly 12 through the lumen defined by retrieval catheter 6 and to an implant site of an IMD. A pull wire (not shown in FIG. 2) may extend from tether handle assembly 13 to tether head assembly 18 through a lumen defined by elongate body 20.

A clinician may advance retrieval catheter 6 through introducer 5 and into the vasculature to the implant site. The clinician may also advance a snare through the catheter, where the snare may be of sufficient length that the clinician may advance a distal end of the snare out of distal opening 11 of cup 8 and attach it to a portion of an IMD implanted in the patient, e.g., by placing a distal loop of the snare around an attachment member of the IMD and drawing the distal loop tight around the attachment member. In some examples, the snare may be used to pull the IMB from the implant site and into cup 8 where it can be safely removed from the body, along with the snare and retrieval catheter. In some examples, the snare may be used to guide cup 8 around the IMD without removing the IMD from the patient's tissue. Once the IMB is within cup 8, the snare may be detached from the IMD and proximally withdrawn from the catheter. Thereafter, the clinician may advance tether head assembly 18 of tether assembly 12 distally through the catheter to cup 8, whereupon the clinician manipulates tether handle assembly 13 to attach an attachment mechanism of tether head assembly 18 to an attachment member of the IMB. In order to align the attachment mechanism of tether head assembly 18 with an attachment member of the IMD, a positioning element may be fixedly positioned over elongate body 20 proximal to tether head assembly 18. Positioning element 22 may be fixedly positioned over elongate body 20 by connecting to tether head assembly 18 or elongate body 20 any of a variety of techniques, such as welding, crimping, threading, reflowing, overmolding, bonding, adhesives, or friction fits. The clinician may use tether head assembly 18 to disengage the IMD from the tissue of the patient and withdraw it along with retrieval catheter 6. In some examples, after the IMD is disengaged from the patient's tissue, the IMD is repositioned and implanted at a new implant site within the patient using retrieval catheter 6, rather than fully withdrawn.

Figure 3:
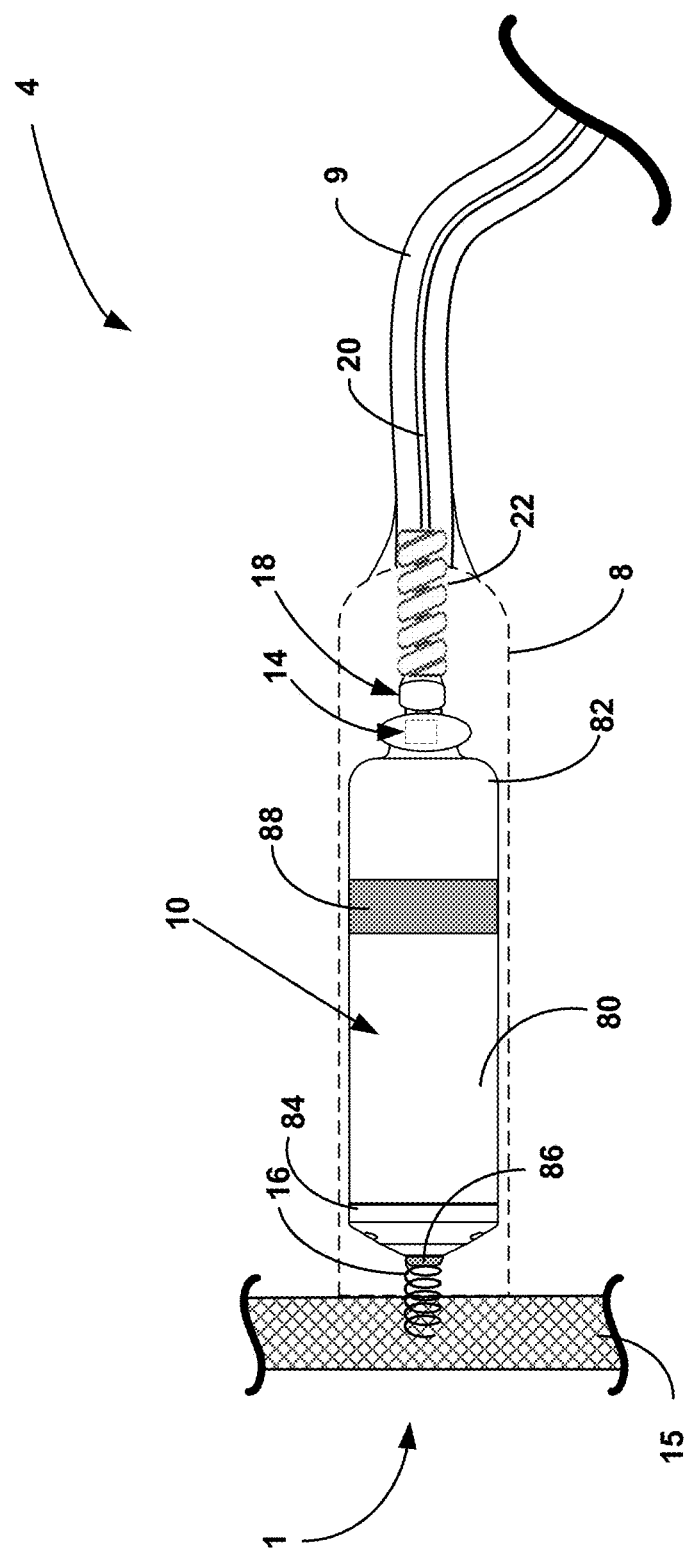
FIG. 3 is a conceptual drawing illustrating, in conjunction with tissue of a heart, a distal portion of the example medical device retrieval system of FIG. 2 retrieving an example IMD.
Figure 4:
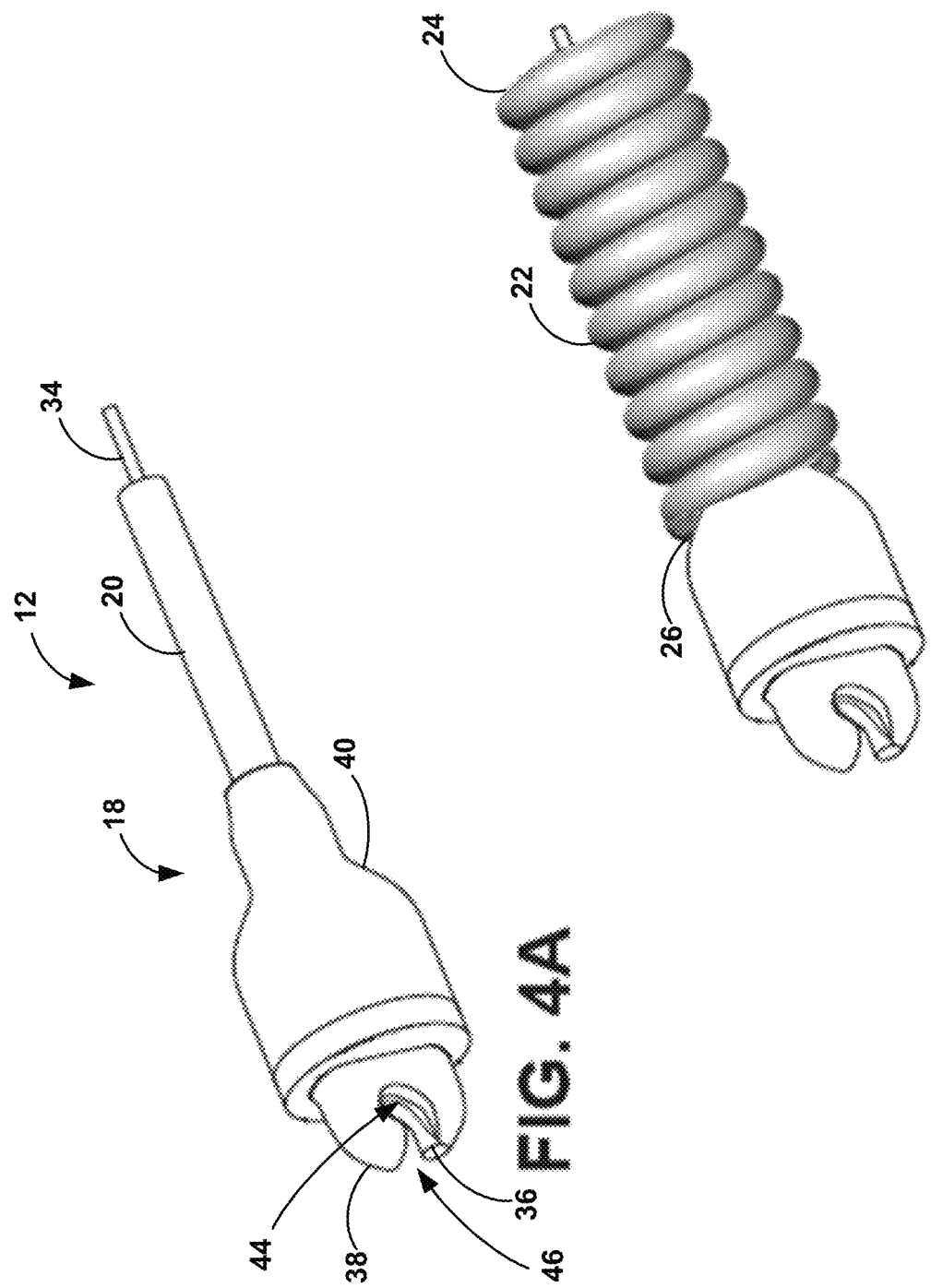
FIG. 4A is a conceptual drawing of a distal portion of an example tether assembly including a tether head assembly and an elongate member.
FIG. 4B is conceptual drawing of a distal portion of the example tether assembly of 4A including a positioning element.

FIG. 3 is a conceptual drawing illustrating, in conjunction with tissue 15 of heart 1, a distal portion of the example medical device retrieval system of FIG. 2 retrieving an example IMD 10. IMD 10 may be a pacemaker device having a housing 80 that contains electronic components suitable for performing a variety of pacing functions. However, IMDs configured to deliver other types of electrical therapy to a patient may be adapted for use with retrieval system 4. IMD 10 may include an attachment member 14 at a proximal end thereof and fixation members 16 at a distal end thereof. Tether head assembly 18 may be configured to receive and retain attachment member 14, as further discussed below with respect to FIGS. 4A-5.

In some examples, IMD 10 may include a hermetically sealed housing 80 defining a proximal end 82 and a distal end 84. Housing 80 may contain a pulse generator and an associated power supply (not shown) and an electrode 86, which may be positioned at distal end 84 of housing 80 and which may be electrically coupled to the pulse generator of IMD 10 via a hermetically sealed feedthrough assembly (not shown). Housing 80 may be formed from any suitable biocompatible and biostable metal. For example, housing 80 may be formed from titanium and may be overlaid with an insulative layer (e.g., a medical grade polyurethane, parylene, or silicone). In some examples, IMD 10 may include a housing electrode 88, which may be formed by removing a portion of the insulative layer to expose a metallic surface defined by housing 80. In such examples, housing electrode 88 of IMD 10 may function in conjunction with electrode 86, such as for bipolar pacing and sensing. In some examples, fixation member 16 may be an extension of electrode 86 and may pierce the tissue of the patient to hold IMD 10 in place at the implant site.

Fixation member 16 of IMD 10 may be configured to embed into tissue 15 but be removable through application of a specific force. For example, fixation member 16 may comprise a screw-shaped fixation structure that may be rotated out of tissue at an implant site. While IMD 10 is shown having fixation member 16 that includes a screw-shaped fixation structure (helix), it should be understood that IMD 10 may include any other suitable fixation structure or structures, such as a plurality of tine structures.

A clinician may position the distal portion of a medical device retrieval system in close proximity with an IMD 10 using a snare or similar retrieval mechanism. For example, a clinician may advance retrieval catheter 6 towards the implant site in tissue 15 until a distal end of catheter 6 is in close proximity to IMD 10. In some examples, retrieval catheter 6 may comprise a cup 8 on a distal end of shaft 9, where the interior of cup 8 is in fluid communication with a lumen defined by shaft 9, as shown in FIG. 3. A clinician may advance retrieval catheter 6 distally towards the implant site until the distal opening 11 of cup 8 is in close proximity to IMD 10. The distal end of a shaft of retrieval catheter 6, or distal opening 11 may be in close proximity with IMD 10, when an attachment mechanism of tether head assembly 18 may reach and attach to IMD 10 when extended distally out of the lumen defined by shaft 9. Then the clinician may advance a snare through the catheter shaft. The clinician may attach the distal end of the snare to one or more members or portions of IMD 10 (e.g., the attachment member 14, shroud 90), apply tension to the snare, and advance cup 8 over at least a portion of IMD 10, through distal opening 11, using the snare as a guide.

FIG. 3 illustrates the distal end of cup 8 of retrieval catheter 6 pressed against tissue 15 at the implant site of heart 1. When a clinician is satisfied with the positioning of cup 8 with respect to tissue 15, e.g., that a longitudinal axis of cup 8 is generally orthogonal to a plane defined by tissue 15, and that cup 8 is pressed sufficiently against/into tissue 15 such that fixation member 16 of IMD 10 can be disengaged from the tissue, the clinician may detach the snare from IMD 10 and remove the snare from retrieval catheter 6. In some examples, cup 8 may not need to be pressed against tissue 15, and it may be sufficient for removal of IMD 10 that only a portion of IMD 10 is within cup 8. The clinician may replace the snare with tether assembly 12, including positioning element 22, and advance tether head assembly 18 towards distal cup 8 using tether assembly 12, e.g., by using tether assembly handle 13 to advance tether assembly 12 distally relative to retrieval catheter 6. In some examples, the physician may use a snare in conjunction with tether assembly 12, including positioning element 22, and need not remove and replace the snare before advancing tether assembly 12.

Once tether head assembly 18 reaches the distal end of elongated shaft 9, a clinician may advance tether head assembly 18 distally out of elongated shaft 9 and into cup 8. Positioning element 22 aligns an attachment mechanism of tether head assembly 18 to attachment member 14 while clinician attaches the attachment mechanism of tether head assembly 18 to attachment member 14 of IMD 10. Thereafter, the clinician may be able to disengage IMD 10 from the implant site and move tether assembly 12 proximally, as described in greater detail below, withdrawing retrieval catheter 6, tether assembly 12, and IMD 10 from the patient through introducer 5. In some examples, after IMD 10 is disengaged from the implant site, IMD 10 is repositioned and implanted at a new implant site within the patient using retrieval catheter 6, rather than fully withdrawn.

In some examples, the attachment mechanism of tether head assembly 18 may be configured to automatically latch on to attachment member 14, e.g., via distal advancement of tether head assembly 18 against attachment member 14. In other examples, the clinician may need to operate attachment mechanism of tether head assembly 18 by manipulation of an actuator of tether handle assembly 18. For example, tether assembly 12 may include a pull wire 34 (not shown in FIG. 3) as discussed in further detail with respect to FIG. 4A. Pull wire 34 may be attached at a distal end thereof to tether head assembly 18 and attached at a proximal end thereof to tether handle assembly 13.

The clinician may apply force to an actuator of tether handle assembly 13 to cause tether head assembly 18 to move from a closed position to an open position. In a closed position, attachment member 14 may either be retained within tether head assembly 18 or prevented from entering or attaching to tether head assembly 18. In an open position, attachment member 14 may be attached to or released from tether head assembly 18. With tether head assembly 18 in the open position, the clinician may distally move tether assembly 12 to releasably attach tether head assembly 18 to attachment member 14. In some examples, the attachment mechanism of tether head assembly 18 may be able to open when force is applied to the attachment mechanism in one direction, but not another. For example, the clinician may secure attachment member 14 of IMD 10 to tether head assembly 18 by pressing attachment member 14 into a passageway defined by tether head assembly 18, thereby opening tether head assembly 18 from a first (e.g., closed) position to a second (e.g., open) position and advancing attachment member 14 through the passageway until attachment member 14 is received within a receptacle defined by tether head assembly 18, as further discussed below with respect to FIGS. 4A-5. Once attachment member 14 is fully within the receptacle, the attachment mechanism of tether head assembly 18 may automatically return to the closed position. This may be accomplished by one clinician instead of the two clinicians that may be required to secure an attachment member of an IMD to a tether assembly in some other example medical device retrieval systems. Thus, tether assembly 12 may reduce the time and complexity associated with a procedure to deliver and/or retrieve IMD 10. In some examples, tether head assembly 18 may reduce a possibility of contamination of the medical device or other objects within the surgical field, relative to such other tether assemblies, by reducing the number of people that touch IMD 10 and tether head assembly 18.

As described herein, a clinician may secure attachment member 14 of IMD 10 to tether head assembly 18 at the time of a medical procedure to retrieve IMD 10. In addition, the clinician may release IMD 10 from tether head assembly 18 without cutting a portion of tether assembly 12. In some examples, tether head assembly 18 thus may reduce or eliminate drawbacks that may be associated with other types of tether mechanisms, such as tension associated with pulling on such other tether mechanisms (e.g., a loop of string or similar material), potential twisting or binding of such other tether mechanisms, or the like. The re-usability of tether assembly 12 may mitigate shelf-life considerations with respect to tether assembly 12, retrieval system 4, and IMD 10, such as in examples in which IMD 10 includes a drug eluting component with a finite shelf life. For example, tether assembly 12 and/or retrieval system 4 may not necessarily be associated with a finite shelf life when packaged separately from IMD 10.

FIGS. 4A and 4B are conceptual drawings of a distal portion of tether assembly 12 including tether head assembly 18 and elongate member 20. FIG. 4A and FIG. 4B respectively illustrate the distal portion of tether assembly 12 without and with positioning element 22.

As illustrated in FIG. 4A, elongate body 20 may include a shaft defining a lumen (not shown) in which at least a portion of a pull wire 34 is received. Tether head assembly 18 may include inner retainer 36, an outer retainer 38, and a sheath 40. Components of tether assembly 12 may be separately formed of any suitable material. In some examples, one or more of pull wire 34, inner retainer 36, outer retainer 38, sheath 40, and/or one or more layers of elongate body 20 may be formed of an electrically conductive material, which may help enable testing of placement of IMD 10 during a procedure to deliver IMD 10 (and/or retrieve IMD 10, e.g., based on the result of such placement testing or other testing), as discussed above with respect to FIG. 3. One or more components of tether assembly 12 may be manufactured via a technique such as metal injection molding or any other suitable technique.

Inner retainer 36 may be coupled to pull wire 34 and extends distally from a distal end (not shown) of pull wire 34. Outer retainer 38 defines an aperture that includes a receptacle 44 dimensioned to receive attachment member 14 of IMD 10 through passageway 46. When inner retainer 36 is in a first position, passageway 46 may be dimensioned to prevent passage of attachment member 14 of IMD 10 (e.g., is too narrow to allow passage of attachment member 14, either into or out of receptacle 44, or both).

Proximal movement of pull wire 34 may cause movement of inner retainer 36 from the first position to a second position in which inner retainer 36 does not extend into passageway 46. Additionally, or alternatively, an application of force to inner retainer 36, e.g., to a distal end of inner retainer 36, by attachment member 14 of IMD 10 may cause inner retainer 36 to move from the first position to the second position. With inner retainer 36 in the second position, passageway 46 may be dimensioned to receive attachment member 14 and allow attachment member 14 to pass therethrough. Inner retainer 36 and outer retainer 38 may be received within sheath 40, which may help retain inner retainer 36 within outer retainer 38 and couple outer retainer 38 to elongate body 20.

Tether head assembly 18 may be rotatable around a centerline of the elongate body 20, or of retrieval catheter 6. In this way, tether head assembly 18 may be rotated into the correct orientation in order to attach to attachment member 14 of IMD 10. In some examples, once tether head assembly 18 is attached to attachment member 14, a clinician may rotate tether head assembly, thereby rotating IMD 10 and unscrewing helical fixation member 16 from tissue 15. Accordingly, in such examples tether head assembly 18 is configured to make a torque-transmitting connection to attachment member 14 and IMD 10, and thereby act as a driver to facilitate removal of IMD 10 via unscrewing.

In some examples, tether head assembly 18 and attachment member 14 may depart from the configuration depicted in FIGS. 4A-7. Attachment member 14 may comprise a handle, nut, or other member with a profile which can be gripped on its external perimeter in a manner that facilitates torque transmission between tether head assembly 18 and attachment member 14, and the distal end of tether head assembly 18 can comprise an attachment mechanism in the form of a matching socket which receives attachment member 14 in a closely fitting manner that facilitates torque transmission. In some examples, a physician may attach a snare to attachment member 14 and use the snare to guide the closely fitting socket of the attachment mechanism of tether head assembly 18 around the external perimeter of attachment member 14 to facilitate torque transmission between tether head assembly 18 and IMD 10. In some implementations, attachment member 14 may have an oval profile in a plane orthogonal to its longitudinal axis, and the distal end of tether head assembly 18 can comprise a matching oval socket, or attachment member 14 may have a triangular, square, rectangular, pentagonal, hexagonal, or other polygonal profile, or a notched circular or notched oval profile, or an oblong profile, and tether head assembly 18 can comprise a socket having a matching shape. Optionally, in any of these implementations, attachment member 14 may have a narrowed portion or neck located distal of the aforementioned profile (see, e.g., FIG. 5) to facilitate gripping attachment member 14 via a snare, and/or tether head assembly 18 can incorporate features for receiving and retaining a pin or crossbar of attachment member 14, as discussed elsewhere herein.

In some examples, attachment member 14 may comprise a recess or hole through which the attachment mechanism of tether head assembly 18 may be inserted. The attachment mechanism may comprise a profile which can be gripped on its external perimeter in a manner that facilitates torque transmission between tether head assembly 18 and attachment member 14. Accordingly, in such examples the clinician can make a torque-transmitting connection of tether head assembly 18 to attachment member 14 and IMD 10, and thereby use tether head assembly 18 as a driver to facilitate removal of IMD 10 via unscrewing.

As illustrated by FIG. 4B, positioning element 22 may have a length that defines a distal end 26 and a proximal end 24. The length of positioning element 22 is less than a length of elongate body 20.

Tether head assembly 18 may have an outer diameter sufficiently similar to an inner diameter of elongated shaft 9 that tether head assembly 18 may advance normally through elongated shaft 9 without catching or bending. However, cup 8 may have an inner diameter significantly larger than the outer diameter of tether head assembly 18, such that when tether head assembly 18 is advanced distally out of elongated shaft 9 and into cup 8, elongate body 20 may bend or tilt such that an attachment mechanism of tether head assembly 18 no longer aligns with attachment member 14 of IMD 10. For example, attachment member 14 may be a bar configured to fit into receptacle 44, but when tether head assembly 18 enters cup 8, elongate body 20 may tilt or deflect relative to the centerline of cup 8, pointing passageway 46 away from the bar of attachment member 14.

Positioning element 22 is configured to align the attachment mechanism of tether head assembly 18 with attachment member 14 when tether head assembly 18 extends into cup 8. For example, positioning element 22 may be positioned over sheath 40 and/or elongate body 20, with an outer diameter approximately equal to an inner diameter of elongated shaft 9. As tether head assembly 18 is advanced into cup 8, distal end 26 of positioning element 22 may also advance into cup 8, while proximal end 24 may remain within elongated shaft 9. Positioning element 22 may be firm such that as distal end 26 advances out of elongated shaft 9 and into cup 8, positioning element 22 does not bend, or bends minimally. Although positioning element 22 is described as "firm," it may be flexible enough to bend as it passes through elongated shaft 9 to allow a physician to manipulate tether head assembly 18 with positioning element 22 through elongated shaft 9 to an implant site.

Because proximal end 24 remains within elongated shaft 9, the inner walls of elongated shaft 9 may prevent distal end 26 of the positioning element 22 from leaving a centerline of the elongated shaft, extending radially from the distal end of elongated shaft and into cup 8.

Figure 7B:
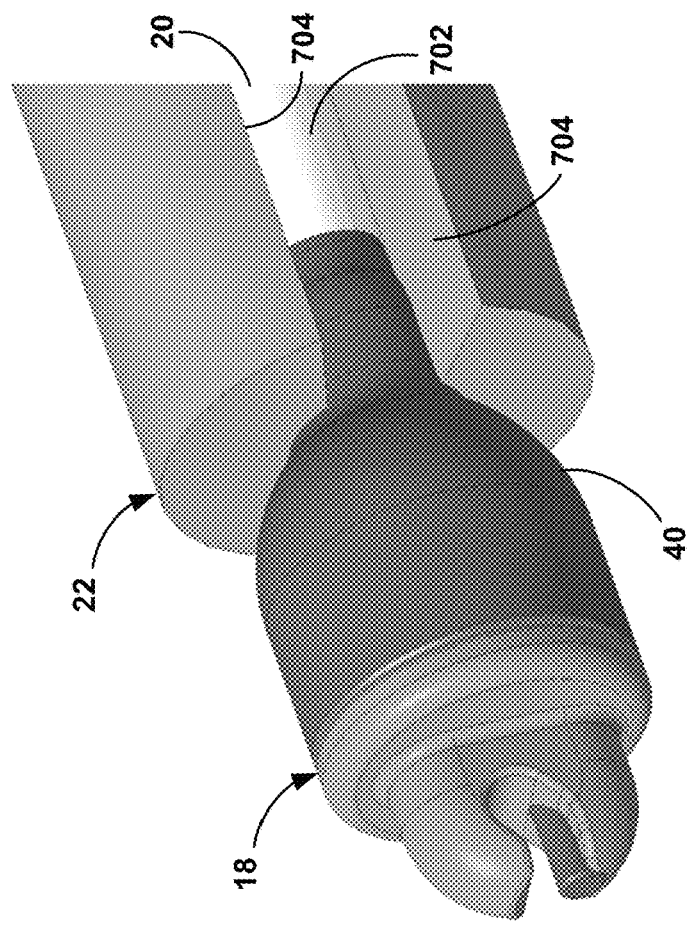
FIG. 7B is a conceptual drawing illustrating an example tether assembly including a tether head assembly and a positioning element according to one embodiment.

Although the example positioning element 22 in FIG. 4B is depicted as a coil, positioning element 22 may take on many forms capable of aligning tether head assembly 18 with attachment member 14. For example, positioning element 22 may comprise a hollow cylinder attached to elongate body 20, where the hollow cylinder has an internal diameter approximately equal to an outer diameter of elongate body 20 and the hollow cylinder has an outer diameter approximately equal to an inner diameter of elongated shaft 9. In another example, as described further in FIG. 7A below, positioning element 22 may comprise a series of fins extending radially away from elongate body 20 until they reach the inner walls of elongated shaft 9. In some examples, positioning element 22 circumferentially encompasses elongate body 20 and/or sheath 40. In some examples, positioning element 22 only surrounds a portion of the circumference of elongate body 20 and/or sheath 40 as shown in FIG. 7B. In another embodiment, positioning element 22 can comprise a proximal extension of tether head assembly 18, e.g., a proximal extension of sheath 40 of tether head assembly 18.

In some examples, as depicted in FIGS. 3-7, positioning element 22 may be configured to align tether head assembly 18 concentrically within elongated shaft 9. In examples wherein the interior of cup 8 is in fluid communication with a lumen defined by shaft 9, the inner diameter of cup 8 is approximately equal to the outer diameter of IMD 10, and the inner diameter of cup 8 is configured to be concentric with the outer diameter of IMD 10 when cup 8 is positioned around IMD 10, wherein attachment member 14 of IMD 10 lies at least partially along the centerline defined by the concentricity. Cup 8 may also be concentric with elongated shaft 9 of retrieval catheter 6, which in turn is concentric with tether head assembly 18, where an attachment mechanism of tether head assembly 18 lies at least partially along the centerline of elongated shaft 9. In this way, when tether head assembly 18 is advanced outward from the distal end of elongated shaft 9 along the centerline of elongated shaft 9 and into cup 8 with the aid of positioning element 22, the attachment mechanism of tether head assembly 18 will align with attachment member 14.

In other examples, cup 8, IMD 10, elongated shaft 9, tether head assembly 18, and positioning element 22 may not share a concentric centerline. In these examples, positioning element 22 may be configured to align the attachment mechanism of tether head assembly 18 with attachment member 14 by compensating for any lack of concentricity between the elements. For example, a lack of concentricity between the aforementioned elements may result in the attachment member 14 of IMD 10 lying one millimeter away from the centerline of elongated shaft 9 as extended into cup 8. However, positioning element 22 may have a shaft spanning its length defining a lumen, where the shaft and lumen are not concentric with an outer diameter of positioning element 22, but where the outer diameter is concentric with elongated shaft 9. A centerline of the lumen may be one millimeter removed from a centerline of the outer diameter, such that positioning element 22 holds a centerline of tether head assembly 18 one millimeter removed from the centerline of elongated shaft 9. In this way, positioning element 22 may align an attachment mechanism of tether head assembly 18 with attachment member 14, both being one millimeter away from the described centerline.

Positioning element 22 may be configured to allow fluid to flow through elongated shaft 9 for treatment of patient through retrieval catheter 6 when positioning element 22 is within the lumen of elongated shaft 9. For example, positioning element 22 may comprise a coil, where each turn of the coil is spaced slightly apart from one another to allow fluid to flow between the turns of the coil. In another example, positioning element 22 may comprise a plurality of channels defining lumens along the length of positioning element 22 from proximal end 24 to distal end 26. These channels may allow fluid to pass from proximal end 24 to distal end 26 and into the body of the patient. In another example, as described below, positioning element 22 may comprise a plurality of fins along the length of positioning element 22 extending radially from an outer diameter of elongate body 20 to an inner diameter of elongated shaft 9, where fluid may flow along the length of positioning element 22 through the gaps in between the fins.

Figure 5:
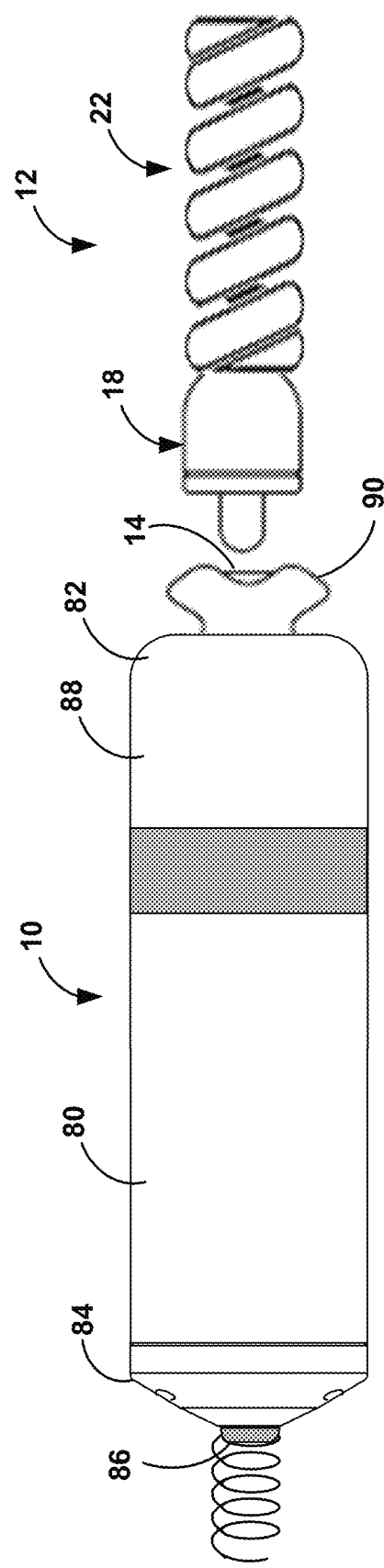
FIG. 5 is a conceptual drawing of the distal portion of the example tether assembly of FIG. 4A-4B in conjunction with a side view of the IMD of FIG. 3, where the tether head assembly and the IMD are not connected.

FIG. 5 is a conceptual drawing of the distal portion of the example tether assembly of FIG. 4A-4B in conjunction with a side view of the IMD of FIG. 3, where the tether head assembly and the IMD are not connected.

FIG. 5 illustrates IMD 10 detached from tether assembly 12, as may be the case prior to removal of IMD 10 from the treatment site. In particular, in FIG. 5, attachment member 14 of IMD 10 is not received within the attachment mechanism of tether head assembly 18 of tether assembly 12.

FIG. 5 illustrates positioning element 22 attached to, or otherwise positioned proximal of, tether head assembly 18 of tether assembly 12 and at least partly covering an elongate body 20 (not pictured in FIG. 5) of tether head assembly 18, wherein elongate body 20 may include a shaft defining a lumen. Pull wire 34 (see, e.g., FIG. 4A) extends through the lumen defined by elongate body 20 and may be connected to inner retainer 36. Various components of retrieval system 12 and tether assembly 18 may be connected by any of a variety of techniques, such as welding, crimping, threading, reflowing, bonding, adhesives, or friction fits. In addition, although positioning element 22 is depicted as connected to tether head assembly, in some examples positioning element 22 may be connected to elongate body 20.

Attachment member 14 of IMD 10 may be included as part of a structure that provides a variety of features supporting a variety of functions related to delivery and retrieval of IMD 10. In the illustrated example, attachment member 14 is formed within, and joined to housing 80 of IMD 10, by a shroud structure 90. In the illustrated example, attachment member 14 comprises a pin, bar, crossbar, or strut that is welded or otherwise fixedly attached to shroud structure 90. Attachment member 14 provides an elongate holding surface that is spaced apart from housing proximal end 82 of housing 80 and that extends along a length substantially orthogonal to a longitudinal axis of IMD 10.

Shroud structure 90 may define a cavity with an opening and attachment member 14 may span and be exposed at the opening. Attachment member 14 may be welded at either end to opposing sides of shroud structure 90. A distal portion of outer retainer 38 of tether head assembly 18 may be configured to enter or otherwise interact with shroud structure 90 (e.g., the cavity thereof) when attachment member 14 is received within passageway 46 and receptacle 44. The configuration of shroud structure 90 and distal portion of outer retainer 38 may selectively inhibit or allow relative motion of IMD 10 and tether assembly in a variety of directions. It should be understood that shroud structure 90 and attachment member 14 are provided for example only, and that a variety of other attachment members may be configured to be attached to tether assemblies.

Figure 6:
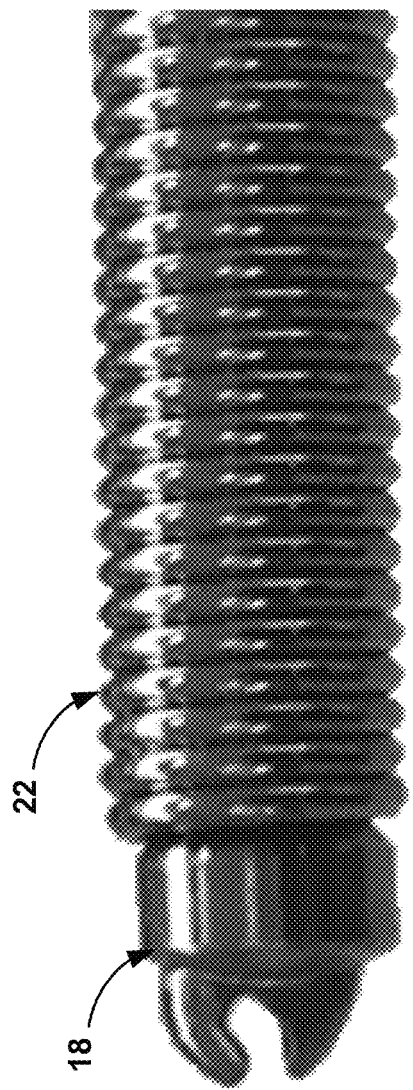
FIG. 6 is a side view of an example tether assembly including a tether head assembly and a positioning element according to one embodiment.

FIG. 6 is a side view of an example tether assembly including a tether head assembly and a positioning element according to one embodiment, which can in some examples be generally similar to the tether head assembly and a positioning element shown in FIG. 4B, except as further described herein.

Positioning element 22 may comprise a coil that extends a length between distal end 26 and proximal end 24, having an inner diameter and an outer diameter. The coil may surround elongate body 20 at a location proximal of and/or adjacent to tether head assembly 18. The inner diameter and/or distal end of positioning element 22 may be connected to tether head assembly 18 and the outer diameter of positioning element 22 may be approximately equal to an outer diameter of at least a portion of tether head assembly 18. The inner diameter of positioning element 22 may define a lumen along the length of positioning element 22, through which a portion of elongate body 20 lies.

The outer diameter of positioning element 22 may be approximately equal to an inner diameter of elongated shaft 9. As tether head assembly 18 and distal end 26 of positioning element 22 extend outwards from the distal end of elongated shaft 9 and into cup 8, proximal end 24 of positioning element 22 may remain within a portion of the distal end of elongated shaft 9. The body of the coil and the close fit of proximal end 24 within elongated shaft 9 may hold distal end 26 of positioning element 22 approximately concentric with elongated shaft 9 while distal end 26 extends into cup 8. In turn, distal end 26 may hold tether head assembly 18 concentric with elongated shaft 9 while tether head assembly 18 extends into cup 8. In this way, positioning element 22 may align tether head assembly 18 with attachment member 14 of IMD 10 within cup 8, where cup 8 and IMD 10 are concentric with elongated shaft 9.

In another example, attachment member 14 does not lie on a centerline of cup 8 or IMD 10. Instead, attachment member 14 may lie a certain distance radially away from the centerline of cup 8, IMD 10. When elongated shaft 9 is concentric with cup 8 or IMD 10, positioning element 22 may hold tether head assembly 18 off the centerline of elongated shaft 9 the same distance and in the same direction as attachment member 14 lies off the centerline of cup 8 or IMD 10. In other examples, IMD 10 may be concentric with cup 8, but elongated shaft 9 may not be concentric with cup 8. In this case, positioning element 22 may hold tether head assembly 18 off the centerline of elongated shaft 9 in a distance and direction to compensate for the lack of concentricity.

In some examples, each turn of the coil of positioning element 22 may be spaced slightly apart from one another to allow fluid to flow between the turns of the coil. In this way, fluid may travel from proximal end 24 to distal end 26 for potential treatment of a patient. In other examples, positioning element 22 may comprise a plurality of channels defining lumens along the length of positioning element 22 from proximal end 24 to distal end 26. These channels may pass through each turn of the coil, allowing fluid to flow through the plurality of channels. Where implemented, this property of allowing fluid flow along the length of positioning element 22 allows positioning element 22 to fit closely within elongated shaft 9 in the radial direction without causing a "piston effect" as positioning element 22 is advanced or retracted along elongated shaft 9. Such a piston effect would entail a buildup of positive fluid pressure on the leading side of positioning element 22 and/or negative fluid pressure on the trailing side.

Figure 7A:
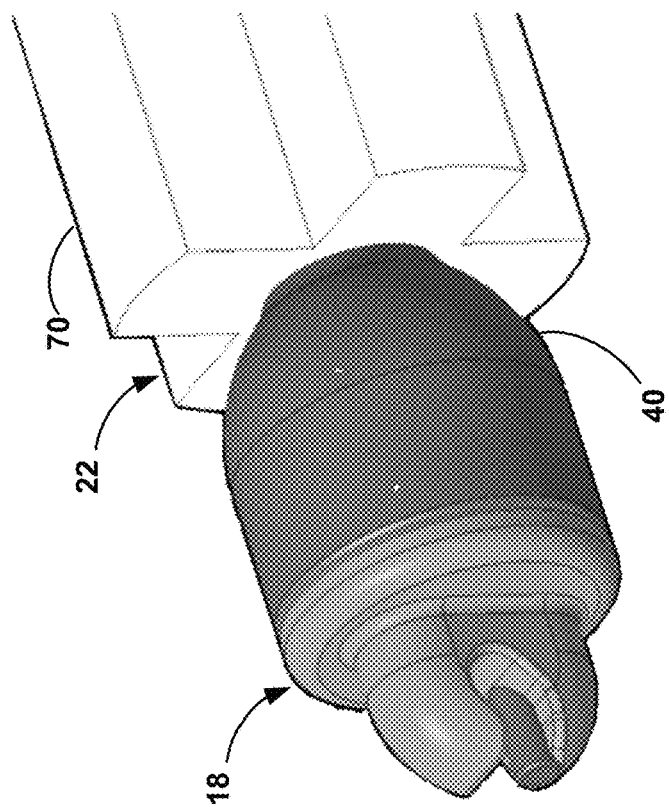
FIG. 7A is a conceptual drawing illustrating an example tether assembly including a tether head assembly and a positioning element according to one embodiment.

FIGS. 7A and 7B are conceptual drawings illustrating example tether assemblies, including a tether head assembly and a positioning element, according to different embodiments.

As illustrated in FIG. 7A, in some examples positioning element 22 may comprise a series of fins 70 (one of which is labeled in FIG. 7) extending along at least a portion of the length of positioning element 22 from proximal end 24 to distal end 26 and extending radially outward from a centerline that travels the length of positioning element 22. Fins 70 may extend radially outward until they reach the inner walls of elongated shaft 9.

In some examples, the edges of fins 70 may join near the center of positioning element 22 such that they define an inner diameter of positioning element 22 that may be connected to tether head assembly 18. The inner diameter of positioning element 22 may be approximately equal to an outer diameter of at least a portion of tether head assembly 18. The inner diameter of positioning element 22 may define a lumen along the length of positioning element 22, through which elongate body 20 extends. The inner diameter of positioning element 22 may surround elongate body 20 at a location proximal of and/or adjacent to tether head assembly 18.

In other examples, fins 70 are individually attached to elongate body 20 at a location proximal of and/or adjacent to tether head assembly 18, and the edges of fins 70 do not join such that they define an inner diameter of positioning element 22. In this case, fins 70 may be attached to tether head assembly or elongate body 20 along a length from proximal end 24 to distal end 26.

Fins 70 of example positioning element 22 may extend radially outward from a centerline of positioning element 22 such that their edges create a profile defining an outer diameter. The outer diameter of positioning element 22 may be approximately equal to an inner diameter of elongated shaft 9. As tether head assembly 18 and distal end 26 of positioning element 22 extend distally from the distal end of elongated shaft 9 and into cup 8, proximal end 24 of positioning element 22 may remain within a portion of the distal end of elongated shaft 9. The close fit of proximal end 24 of fins 70 within elongated shaft 9 may hold distal end 26 of positioning element 22 approximately concentric with elongated shaft 9 while distal end 26 extends into cup 8. In turn, distal end 26 may hold tether head assembly 18 concentric with elongated shaft 9 while tether head assembly 18 extends into cup 8. In this way, positioning element 22 may align tether head assembly 18 with attachment member 14 of IMD 10 within cup 8, where cup 8 and IMD 10 are concentric with elongated shaft 9.

In another example, attachment member 14 does not lie on a centerline of cup 8 or IMD 10. Instead, attachment member 14 may lie a certain distance radially away from the centerline of cup 8, IMD 10. When elongated shaft 9 is concentric with cup 8 or IMD 10, positioning element 22 may hold tether head assembly 18 off the centerline of elongated shaft 9 the same distance and in the same direction as attachment member 14 lies off the centerline of cup 8 or IMD 10. For example, fins 70 on one side of positioning element 22 may be a different length than fins 70 on another side, or each fin of the plurality of fins 70 of positioning element 22 may be a different length such that a centerline of the inner diameter of positioning element 22 lies parallel to, but offset from, a centerline of elongated shaft 9. Positioning element 22 may hold tether head assembly 18 along the offset centerline as well to align tether head assembly 18 with attachment member 14. In other examples, IMD 10 may be concentric with cup 8, but elongated shaft 9 may not be concentric with cup 8. In this case, positioning element 22 may hold tether head assembly 18 off the centerline of elongated shaft 9 in a distance and direction to compensate for the lack of concentricity.

Each fin 70 of the plurality of fins 70 of positioning element 22 may be spaced apart such that the fins 70 define gaps between one another along the length of positioning element 22. In this way, fluid may travel from proximal end 24 to distal end 26 for potential treatment of a patient. Additionally, where implemented, this property of allowing fluid flow along the length of positioning element 22 allows positioning element 22 to fit closely within elongated shaft 9 in the radial direction without causing a "piston effect" as positioning element 22 is advanced or retracted along elongated shaft 9. Such a piston effect would entail a buildup of positive fluid pressure on the leading side of positioning element 22 and/or negative fluid pressure on the trailing side.

As illustrated in FIG. 7B, in some examples positioning element 22 only surrounds a portion of the circumference of elongate body 20 and/or sheath 40 such that an open channel 702 is defined along positioning element 22, e.g., from distal end 26 to proximal end 24, between surfaces 704. Positioning element 22 may comprise an inner diameter approximately equal to an outer diameter of elongate body 20 and an outer diameter approximately equal to an inner diameter of elongated shaft 9.

The material of positioning element 22 may be slightly elastic such that when a force is applied to surfaces 704, open channel 702 grows, and when the force is released, positioning element 22 and open channel 702 return to their original shape and size. In this way, positioning element 22 may act as a clip that a physician may attach to elongate body 20 and/or sheath 40 before inserting tether head assembly into a patient's body.

Fluid may travel from proximal end 24 to distal end 26 through open channel 702 for potential treatment of a patient. Positioning element 22 may comprise a plurality of other channels defining lumens along the length of positioning element 22 from proximal end 24 to distal end 26 as well, allowing fluid flow. Additionally, where implemented, this property of allowing fluid flow along the length of positioning element 22 allows positioning element 22 to fit closely within elongated shaft 9 in the radial direction without causing a "piston effect" as positioning element 22 is advanced or retracted along elongated shaft 9. Such a piston effect would entail a buildup of positive fluid pressure on the leading side of positioning element 22 and/or negative fluid pressure on the trailing side.

Figure 8:
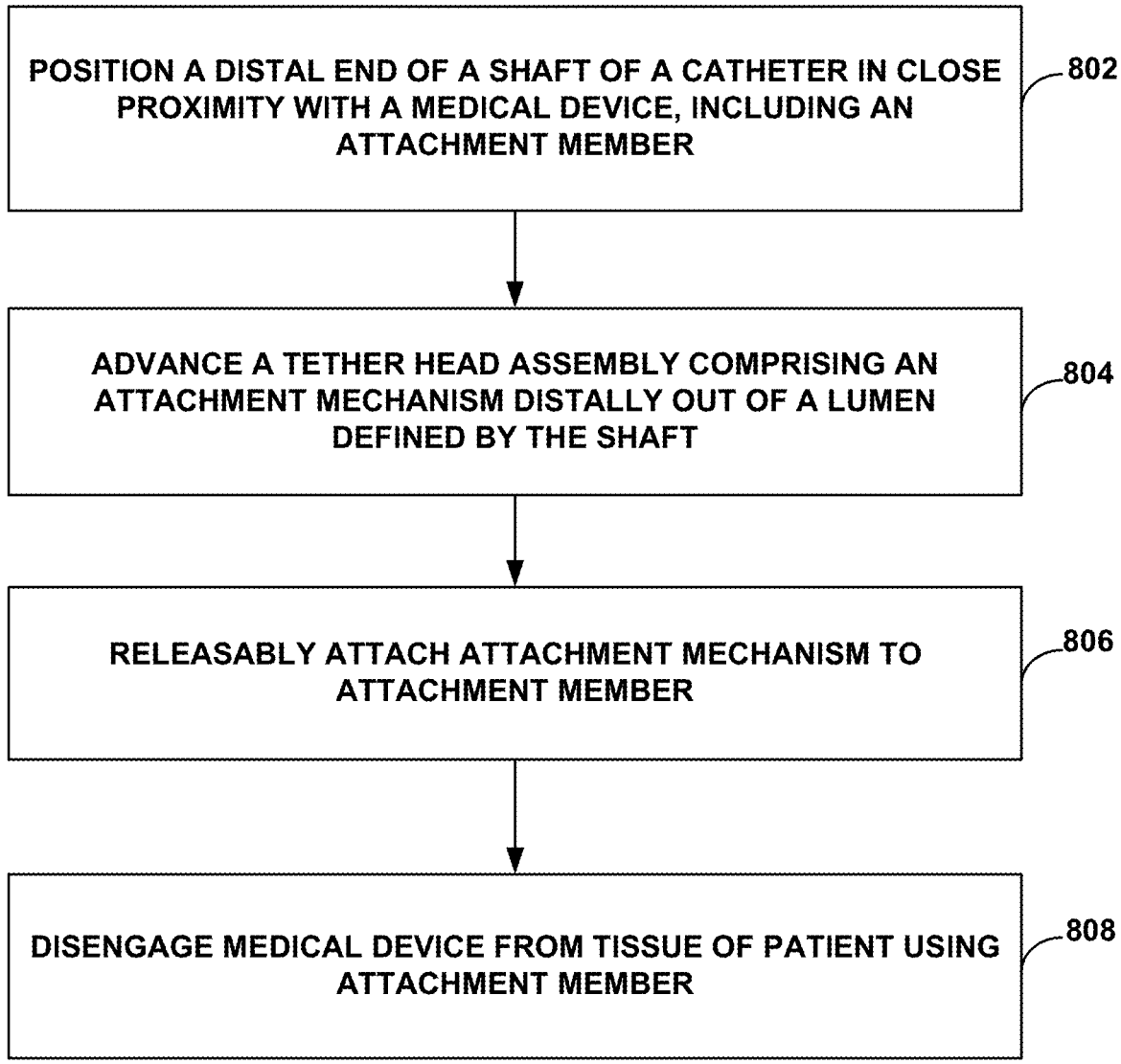
FIG. 8 is a flow diagram illustrating an example process for retrieving an IMD from a location within the heart using the example tether assemblies of FIGS. 4A-7.

FIG. 8 is a flow diagram illustrating an example process for retrieving an IMD from a location within the heart using the example tether assemblies of FIGS. 4A-7.

A medical device retrieval system 4, including a distal end of a shaft of retrieval catheter 6, is positioned in close proximity with IMD 10 (802). A clinician may advance retrieval catheter 6 through introducer 5 and into the vasculature to the implant site. The clinician may advance retrieval catheter 6 towards the implant site in tissue 15 until the distal end of a shaft of retrieval catheter 6 is sufficiently close to IMD 10. In some examples, cup 8 is connected at the distal end of the shaft of retrieval catheter 6, and the clinician may position distal opening 11 of cup 8 sufficiently close to IMD 10. The distal end of a shaft of retrieval catheter 6, or distal opening 11 may be sufficiently close to IMD 10 when a snare advanced through catheter 6 may reach and attach to IMD 10. The clinician may advance the snare through catheter 6 to the implant site. The snare may be of sufficient length that a clinician may advance a distal end of the snare out of distal opening 11 of cup 8 and attach the distal end of the snare to one or more members of IMD 10 (e.g., attachment member 14, shroud 90). The clinician may apply tension to the snare and advance cup 8 over at least a portion of IMD 10, through distal opening 11, using the snare as a guide.

When the clinician is satisfied with the positioning of cup 8 with respect to tissue 15, the clinician may detach the snare from IMD 10 and remove the snare from retrieval catheter 6. The clinician may replace the snare with tether assembly 12, including positioning element 22, advancing tether head assembly 18 towards distal cup 8 using tether assembly 12, e.g., by using tether assembly handle 13 to advance tether assembly 12 distally relative to retrieval catheter 6.

Once tether head assembly 18 reaches the distal end of elongated shaft 9, a clinician may advance tether head assembly 18, including an attachment mechanism of tether head assembly 18, distally out of a lumen defined by elongated shaft 9 (804). Positioning element 22 may be fixedly positioned over tether head assembly 18 and aligns an attachment mechanism of tether head assembly 18 to attachment member 14 while tether head assembly 18 is extended distally out of the lumen. In some examples, tether head assembly may extend distally out of the lumen and into cup 8. In some examples, positioning element 22 may position tether head assembly 18 concentrically within cup 8 while tether head assembly 18 is extended distally out of the lumen and into cup 8. In some examples, proximal end 24 of positioning element 22 may remain inside the lumen defined by elongated shaft 9 while a distal end of tether head assembly 18 is extended distally out of the lumen.

When the attachment mechanism of tether head assembly 18 and attachment member 14 are aligned, clinician attaches the attachment mechanism of tether head assembly 18 to attachment member 14 of IMD 10 (806). In some examples, the attachment mechanism of tether head assembly 18 may be configured to automatically latch on to attachment member 14. In other examples, the clinician may need to operate attachment mechanism of tether head assembly 18 by manipulation of an actuator of tether handle assembly.

The clinician may disengage IMD 10 from the patient's tissue at the implant site (808). In some examples, tether head assembly 18, positioning element 22, and pull wire 34 may be rotatable around a centerline of elongated shaft 9, and fixation member 16 may be helical. The clinician may rotate tether head assembly 18 to unscrew fixation member 16 and IMD 10 from the tissue at the implant site. Accordingly, in such examples the clinician can make a torque-transmitting connection of tether head assembly 18 to attachment member 14 and IMD 10, and thereby use tether head assembly 18 as a driver to facilitate removal of IMD 10 via unscrewing. Once IMD 10 has been disengaged from the patient's tissue, it may be withdrawn from the patient proximally through introducer 5 along with retrieval catheter 6. In some examples, after IMD 10 is disengaged from the patient's tissue, IMD 10 may be repositioned and implanted at a new implant site within the patient using retrieval catheter 6, rather than fully withdrawn, after which retrieval catheter 6 may be withdrawn including tether assembly 12.

Figure 9:
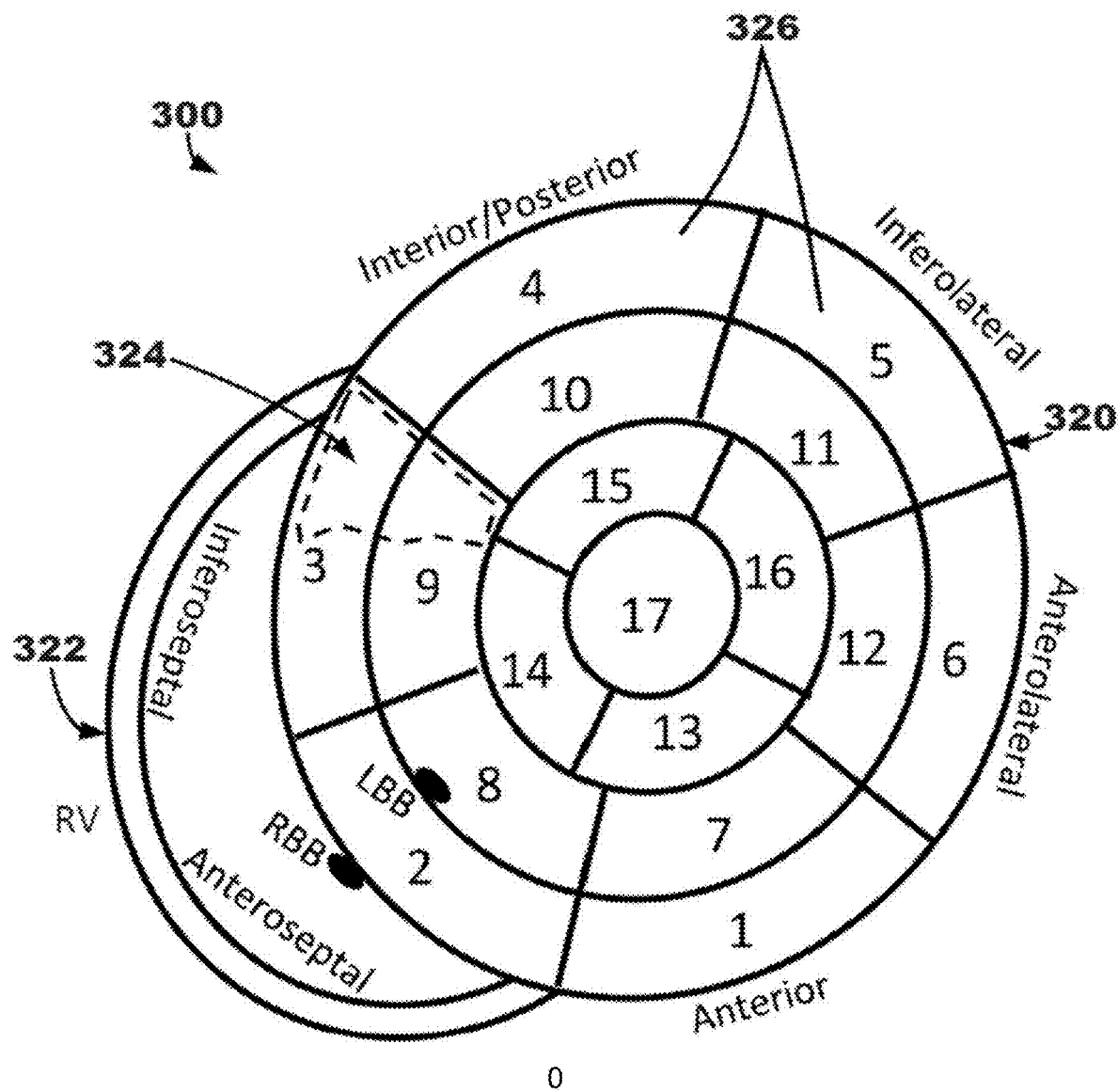
FIG. 9 is a conceptual diagram of a map of a patient's heart in a standard 17 segment view of the left ventricle showing various electrode implantation locations for use with, e.g., the exemplary system and devices of FIGS. 2-7B.

FIG. 9 is a conceptual diagram of a map of a patient's heart in a standard 17 segment view of the left ventricle showing various electrode implantation locations for use with, e.g., the exemplary system and devices of FIGS. 2-7B.

FIG. 9 is a two-dimensional (2D) ventricular map 300 of a patient's heart (e.g., a top-down view) showing the left ventricle 320 in a standard 17 segment view and the right ventricle 322. The map 300 includes a plurality of areas 326 corresponding to different regions of a human heart. As illustrated, the areas 326 are numerically labeled 1-17 (which, e.g., correspond to a standard 17 segment model of a human heart, correspond to 17 segments of the left ventricle of a human heart, etc.). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bunch branch (RBB) and left bundle branch (LBB).

In some embodiments, any tissue-piercing electrode of the present disclosure may be implanted in the basal and/or septal region of the left ventricular myocardium of the patient's heart. In particular, the tissue-piercing electrode may be implanted from the triangle of Koch region of the right atrium through the right atrial endocardium and central fibrous body.

Once implanted, the tissue-piercing electrode may be positioned in the target implant region, such as the basal and/or septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal anteroseptal area 3, mid-anteroseptal area 8, mid-inferoseptal area 9, and apical septal area 14.

In some embodiments, the tissue-piercing electrode may be positioned in the basal septal region of the left ventricular myocardium when implanted. The basal septal region may include one or more of the basal anteroseptal area 2, basal inferoseptal area 3, mid-anteroseptal area 8, and mid-inferoseptal area 9.

In some embodiments, the tissue-piercing electrode may be positioned in the high inferior/posterior basal septal region of the left ventricular myocardium when implanted. The high inferior/posterior basal septal region of the left ventricular myocardium may include a portion of at least one of the basal inferoseptal area 3 and mid-inferoseptal area 9. For example, the high inferior/posterior basal septal region may include region 324 illustrated generally as a dashed-line boundary. As shown, the dashed line boundary represents an approximation of about where the high inferior/posterior basal septal region and may take somewhat different shape or size depending on the particular application. Without being bound by any particular theory, intraventricular synchronous pacing and/or activation may result from stimulating the high septal ventricular myocardium due to functional electrical coupling between the subendocardial Purkinje fibers and the ventricular myocardium.

This disclosure includes the following examples:

Example 1: A system comprising: a catheter comprising an elongated shaft defining a lumen; and a tether assembly comprising: an elongate body; a tether head assembly attached to a distal end of the elongate body, the tether head assembly comprising an attachment mechanism configured to releasably attach to an attachment member of a medical device; and a positioning element fixedly positioned over the elongate body and configured to align the attachment mechanism with the attachment member when the tether head assembly is extended distally out of the lumen, wherein the positioning element comprises: a distal end; a proximal end; a length between the distal end and proximal end that is less than a length of the elongate body; and wherein the tether head assembly, elongate body, and positioning element are movable within the lumen of the elongated shaft.

Example 2: The system of example 1, wherein the positioning element is configured to position the tether head assembly concentrically with the elongated shaft.

Example 3: The system of example 1 or example 2, wherein the catheter comprises a cup on a distal end of the shaft, an interior of the cup in fluid communication with the lumen, and wherein: the positioning element is configured to position the tether head assembly concentrically with the cup when the tether head assembly and positioning element are at least partially extending into the cup from a distal end of the elongated shaft.

Example 4: The system of any of examples 1 to 3, wherein elongate body comprises a pull wire and the tether assembly further comprises a tether handle assembly attached to a proximal end of the pull wire, wherein the tether handle assembly is configured to cause the movement of the pull wire along the catheter centerline.

Example 5: The system of any of examples 1 to 4, wherein the tether head assembly is rotatable around a centerline of the catheter.

Example 6: The system of any of examples 1 to 5, wherein the positioning element comprises an inner diameter approximately equal to at least a portion of an outer diameter of the tether head assembly or the elongate body, and wherein the positioning element comprises an outer diameter approximately equal to an inner diameter of the catheter that defines the lumen.

Example 7: The system of any of examples 1 to 6, wherein the positioning element comprises a coil.

Example 8: The system of example 6, wherein the positioning element comprises a hollow cylinder.

Example 9: The system of any of examples 1 to 5, wherein the positioning element further comprises: an inner diameter; and a plurality of fins along the length wherein each fin of the plurality of fins extends from the inner diameter a distance approximately to an inner surface of the catheter that defines the lumen.

Example 10: The system of any of examples 1 to 9, wherein the positioning element further comprises a plurality of channels along the length of the positioning element configured to allow a fluid to flow through the lumen of the catheter when the positioning element is within the lumen of the catheter.

Example 11: The system of any of examples 1 to 10, wherein the proximal end of the positioning element remains inside the elongated shaft of the catheter when a distal end of the tether head assembly is extended distally out of the lumen.

Example 12: The system of any of examples 1 to 11, wherein the positioning element is positioned over the elongate body proximate to the tether head assembly.

Example 13: The system of any of examples 1 to 12, wherein:

the catheter is configured to implant the medical device at a location within the patient; and the catheter is configured to withdraw the medical device from the location within the patient.

Example 14: The system of any of examples 1 to 13, wherein the attachment mechanism comprises a drive member configured to be inserted into the attachment member such that the attachment member may grip the attachment mechanism in a manner that facilitates torque transmission between the tether head assembly and the attachment member.

Example 15: The system of any of examples 1 to 14, wherein: the attachment member comprises a profile with an external perimeter; and the attachment mechanism comprises a socket that fits over the profile such that the attachment mechanism may grip the attachment member on the external perimeter in a manner that facilitates torque transmission between the tether head assembly and the attachment member.

Example 16: A method comprising: positioning a distal end of a shaft of a catheter in close proximity with at least a portion of a medical device, including an attachment member; advancing a tether head assembly of a tether assembly distally out of a lumen defined by the shaft, wherein the tether head assembly comprises an attachment mechanism, and wherein the tether assembly comprises: an elongate body; and the tether head assembly at a distal end of the elongate body; and a positioning element positioned over the elongate body and configured to align the attachment mechanism with the attachment member when the tether head assembly is extended distally out of the lumen, wherein the positioning element comprises: a distal end; a proximal end; a length between the distal end and proximal end that is less than a length of the elongate body; releasably attaching an attachment mechanism of the tether head assembly to the attachment member of the medical device; and disengaging the medical device from tissue of a patient using the attachment member.

Example 17: The method of example 16, wherein disengaging the medical device comprises rotating the attachment member to unscrew the medical device from the tissue.

Example 18: The method of example 16 or example 17, wherein: the catheter comprises a cup on a distal end of the shaft, an interior of the cup in fluid communication with the lumen; positioning a distal end of a shaft of a catheter in close proximity with at least a portion of a medical device comprises positioning at least a portion of the cup around the medical device; and the positioning element is configured to position the tether head assembly concentrically with the cup while the tether head assembly is being advanced out of the lumen and into the cup.

Example 19: The method of any of examples 16-18, wherein the proximal end of the positioning element remains inside the elongated shaft of the catheter when a distal end of the tether head assembly is extended distally out of the lumen.

Example 20: The method of any of examples 16-19, further comprising implanting the medical device in the patient using a system comprising the catheter and the tether assembly.

Various aspects of the disclosure have been described. These and other aspects are within the scope of the following claims.

What is claimed is:

1. A system comprising:
a catheter comprising an elongated shaft defining a lumen; and a tether assembly comprising:
an elongate body;
a tether head assembly attached to a distal end of the elongate body, the tether head assembly comprising an attachment mechanism configured to releasably attach to an attachment member of a medical device; and
a positioning element fixedly positioned over the elongate body and configured to align the attachment mechanism with the attachment member when the tether head assembly is extended distally out of the lumen, wherein the positioning element comprises:
a distal end;
a proximal end; and
a length between the distal end and proximal end that is less than a length of the elongate body; and
wherein the tether head assembly, elongate body, and positioning element are movable within the lumen of the elongated shaft.

2. The system of claim 1, wherein the positioning element is configured to position the tether head assembly concentrically with the elongated shaft.

3. The system of claim 1, wherein the catheter comprises a cup on a distal end of the shaft, an interior of the cup in fluid communication with the lumen, and wherein:
the positioning element is configured to position the tether head assembly concentrically with the cup when the tether head assembly and positioning element are at least partially extending into the cup from a distal end of the elongated shaft.

4. The system of claim 1, wherein the elongate body comprises a pull wire and the tether assembly further comprises a tether handle assembly attached to a proximal end of the pull wire, wherein the tether handle assembly is configured to cause movement of the pull wire along the catheter centerline.

5. The system of claim 1, wherein the tether head assembly is rotatable around a centerline of the catheter.

6. The system of claim 1, wherein the positioning element comprises an inner diameter approximately equal to at least a portion of an outer diameter of the tether head assembly or the elongate body, and wherein the positioning element comprises an outer diameter approximately equal to an inner diameter of the catheter that defines the lumen.

7. The system of claim 1, wherein the positioning element comprises a coil.

8. The system of claim 6, wherein the positioning element comprises a hollow cylinder.

9. The system of claim 1, wherein the positioning element further comprises:
an inner diameter; and
a plurality of fins along the length wherein each fin of the plurality of fins extends from the inner diameter a distance approximately to an inner surface of the catheter that defines the lumen.

10. The system of claim 1, wherein the positioning element further comprises a plurality of channels along the length of the positioning element configured to allow a fluid to flow through the lumen of the catheter when the positioning element is within the lumen of the catheter.

11. The system of claim 1, wherein the proximal end of the positioning element remains inside the elongated shaft of the catheter when a distal end of the tether head assembly is extended distally out of the lumen.

12. The system of claim 1, wherein the positioning element is positioned over the elongate body proximate to the tether head assembly.

13. The system of claim 1, wherein:
the catheter is configured to withdraw the medical device from a location within a patient.

14. The system of claim 1, wherein the attachment mechanism comprises a drive member configured to be inserted into the attachment member such that the attachment member may grip the attachment mechanism in a manner that facilitates torque transmission between the tether head assembly and the attachment member.

15. The system of claim 1, wherein:
the attachment member comprises a profile with an external perimeter; and
the attachment mechanism comprises a socket that fits over the profile such that the attachment mechanism may grip the attachment member on the external perimeter in a manner that facilitates torque transmission between the tether head assembly and the attachment member.

16. A method comprising:
positioning a distal end of a shaft of a catheter in close proximity with at least a portion of a medical device, including an attachment member;
advancing a tether head assembly of a tether assembly distally out of a lumen defined by the shaft, wherein the tether head assembly comprises an attachment mechanism, and wherein the tether assembly comprises:
an elongate body; and
the tether head assembly at a distal end of the elongate body; and
a positioning element positioned over the elongate body and configured to align the attachment mechanism with the attachment member when the tether head assembly is extended distally out of the lumen, wherein the positioning element comprises:
a distal end;
a proximal end; and
a length between the distal end and proximal end that is less than a length of the elongate body;
releasably attaching an attachment mechanism of the tether head assembly to the attachment member of the medical device; and
disengaging the medical device from tissue of a patient using the attachment member.

17. The method of claim 16, wherein disengaging the medical device comprises rotating the attachment member to unscrew the medical device from the tissue.

18. The method of claim 16, wherein:
the catheter comprises a cup on a distal end of the shaft, an interior of the cup in fluid communication with the lumen;
positioning a distal end of a shaft of a catheter in close proximity with at least a portion of a medical device comprises positioning at least a portion of the cup around the medical device; and
the positioning element is configured to position the tether head assembly concentrically with the cup while the tether head assembly is being advanced out of the lumen and into the cup.

19. The method of claim 16, wherein the proximal end of the positioning element remains inside an elongated shaft of the catheter when a distal end of the tether head assembly is extended distally out of the lumen.

20. The method of claim 16, further comprising implanting the medical device in the patient using a system comprising the catheter and the tether assembly.

* * * * *